US008067170B2

(12) United States Patent
Chakrabarty (10) Patent No.: US 8,067,170 B2
(45) Date of Patent: *Nov. 29, 2011

(54) BINDING METHOD AND APPARATUS FOR SORTING OBJECTS

(75) Inventor: Tania Chakrabarty, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/232,164

(22) Filed: Sep. 11, 2008

(65) Prior Publication Data

US 2009/0068671 A1   Mar. 12, 2009

Related U.S. Application Data

(60) Provisional application No. 60/960,004, filed on Sep. 11, 2007, provisional application No. 60/960,059, filed on Sep. 13, 2007.

(51) Int. Cl.
*C12Q 1/68* (2006.01)
(52) U.S. Cl. ........................................................ 435/6.1
(58) Field of Classification Search .................. None
See application file for complete search history.

(56) References Cited

U.S. PATENT DOCUMENTS

| | | | | |
|---|---|---|---|---|
| 5,436,157 A * | 7/1995 | Herr et al. | ............... | 435/252.33 |
| 5,629,147 A * | 5/1997 | Asgari et al. | .................... | 435/5 |
| 6,540,895 B1 | 4/2003 | Spence et al. | | |
| 6,863,406 B2 | 3/2005 | Grier et al. | | |
| 7,402,131 B2 * | 7/2008 | Mueth et al. | ..................... | 494/36 |
| 2002/0182751 A1 * | 12/2002 | Herr et al. | ..................... | 436/526 |
| 2003/0215845 A1 * | 11/2003 | Bille | ................ | 435/6 |
| 2005/0130173 A1 | 6/2005 | Leamon et al. | | |
| 2005/0244879 A1 | 11/2005 | Schumm et al. | | |
| 2005/0255606 A1 | 11/2005 | Ahmed et al. | | |
| 2006/0008823 A1 * | 1/2006 | Kemp et al. | ..................... | 435/6 |
| 2006/0134603 A1 | 6/2006 | Plewa et al. | | |
| 2006/0228758 A1 * | 10/2006 | Muchhal et al. | ............... | 435/7.1 |
| 2007/0029257 A1 | 2/2007 | Mueth et al. | | |
| 2007/0077570 A1 | 4/2007 | Lao et al. | | |

OTHER PUBLICATIONS

Hendrickson et al. (Nucleic Acids Res. Feb. 11, 1995;23(3):522-9).*

* cited by examiner

*Primary Examiner* — Christopher M. Babic
(74) *Attorney, Agent, or Firm* — Jean C. Edwards, Esq.; Edwards Neils PLLC (57) ABSTRACT

The present invention relates to a method and apparatus of sorting objects including, providing a sample having wanted objects and unwanted objects; coating a surface of a sample holder with an antibody; placing an eluted sample on the sample holder; binding an antigen in the wanted objects with the antibody on the surface of the sample holder to sort the objects into wanted objects and unwanted objects; separating the wanted objects; and performing PCR-based STR analysis on the wanted objects. In one embodiment, holographic optical trapping is used to further sort the wanted objects. In other embodiments, the wanted objects are sperm and the antibody is a human sperm specific antibody, and the PCR is single cell PCR-based STR analysis. In still other embodiments, the binding is direct or indirect, ligands are used to bind to object-specific organomolecules, and protein A or protein G are used to bind the antibody.

27 Claims, 5 Drawing Sheets

BINDING METHOD AND APPARATUS FOR SORTING OBJECTS

The present application claims priority from U.S. Provisional Patent Applications No. 60/960,004, filed Sep. 11, 2007, and 60/960,059, filed Sep. 13, 2007, the contents of both of which are herein incorporated by reference in their entirety.

BACKGROUND OF THE INVENTION

1. Field of the Invention

The present invention relates to methods and apparatuses for sorting objects in DNA analysis. More particularly, the present invention relates to the sorting of sperm in a binding method using antibody or other sperm-recognizing biomolecules, and an apparatus thereof. In one embodiment, a polymerase chain reaction (PCR) method is performed after the objects are sorted—in some cases, a single cell PCR method—to identify persons/assailants in sexual assault cases in forensic DNA analysis, or for other applications in medical diagnostics.

2. Description of the Related Art

In conventional forensic DNA analysis, specimens are commonly matched to alleged criminal suspects in modern law enforcement, using human identification systems commonly based on short tandem repeats (STR) analysis which involve the amplification of the query DNA by polymerase chain reaction (PCR). PCR is a powerful tool which allows for replicating/amplifying trace amounts of DNA fragments into quantities that can be analyzed in a meaningful way. This technology has been adapted for DNA sequencing, DNA fingerprinting etc., and has the ability to detect specific DNA fragments in samples.

Thus, forensic DNA analysis is accomplished using the high power of discrimination and rapid analysis speed of STR markers in the human genome, and has now become the most popular method of choice in forensic DNA analysis.

Although STR analysis is commonly used, it suffers from several pitfalls, the most significant of which arises from contamination of the DNA samples prior to PCR (Polymerase Chain Reaction) based STR analysis, and the time it takes to perform the entire STR analysis on a given sample.

For example, the DNA to be analyzed for STRs from sexual assault evidence should ideally come from the sperm of the assailant. However, the sperm sample is often commonly contaminated with (1) epithelial cells lining the vagina, and occasionally, with (2) epithelial cells from the mouth (buccal cells), and (3) cells from the skin, as well as cells in the urine sample. One might also expect to see erythrocytes, neutrophils, foam cells (non-descript epithelial cells), etc., in sexual assault crime scene samples as well.

Thus, it is clear that better and more accurate STR analysis will be achieved if the sperm cells could be separated from any or all of the contaminating cells before PCR is performed.

Commonly used methods of differential extraction cannot completely separate male (assailant) sperm and female (victim) epithelial cell DNA in a forensic sample. For example, initial lysis using reductant free solution, lyses epithelial cells (the most common contaminant in a sexual assault forensic sample), and leaves sperm cells intact for effective separation of DNA fractions. However, differential lysis causes immature sperm cell lysing thereby causing unwanted DNA to be coamplified along with the query DNA (from sperm alone). This leads to mixed STR profile generation which are hard to analyze and cannot identify a unique individual. Such problems in STR analysis causes 50% of the STR analysis based human identification to fail.

In addition, another limitation in solving forensic cases comes from the limited availability of cells for analysis. This may be due to limited evidence samples being present, degradation of the DNA and cell samples in general over time, and/or the presence of very few sperm cells in a sexual assault crime sample, to be able to solve the case based on standard PCR.

Thus, a method that would prevent or alleviate the above problems is desired.

SUMMARY OF THE INVENTION

The present invention relates to methods and apparatuses for sorting objects using a binding method, using antibody or other sperm-recognizing biomolecules, in DNA analysis, and specifically relates to separating sperm from non-sperm contaminants.

In one embodiment, an antibody that recognizes sperm is coated on a substrate to sort and separate sperm from other contaminants. In general, one method which can operate either in stand-alone mode or in conjunction with holographic optical trapping to separate sperm from contaminating cells, is to use an antibody-coated substrate where the antibody selectively recognizes a surface antigen on the human sperm, for example.

Alternatively, another choice of antibody could be one that targets the H—Y antigen typically found on male determining spermatozoa.

In another embodiment, the antibody on the substrate could be an anti-immunoglobulin antibody which in turn recognizes the monoclonal antibody targeted against the sperm specific surface antigen. This involves first using a sperm specific antibody to recognize and bind to sperm in a forensic sample and subsequently allows the antibody labeled sperm to be recognized and captured by anti-immunoglobulin.

In cases where very few sperm are present in a forensics sample containing other contaminating cells, one can even use multiple sperm specific antibodies in tandem to select and sort the sperm for downstream analysis.

Standard bioconjugation chemistries are available for attaching antibodies on a substrate which can be glass or other materials like plastic. Also this invention can be utilized on substrates of varying geometries such as a flat substrate (in single or multi well format) or a curved surface such as that of an Eppendorf tube. Antibody conjugation on the substrate can be via utilization of common covalent or non-covalent linkage or via adsorption.

One can also envision an extension of this technique to use beads in sperm sorting where instead of coating a substrate with the antibody/antibodies, one utilizes antibody coated beads such as those made of silica, polystyrene or magnetic beads to recognize and bind sperm.

The antibodies which can be utilized to target sperm antigens can be full length or cleaved or even short peptides that recognize the epitope on the sperm surface. In another embodiment that relies on binding sperm but does not involve antibody based sperm recognition, is one where one uses binding partners of the sperm surface receptors to capture sperm from a mixed cell sample.

The present invention will resolve the long-standing problem of co-amplification of female DNA in the sperm cell fraction which has been suggested to occur in ~40% of forensic samples relevant to sexual assault (see Korf B R, in "Current Protocols in Human Genetics", Wiley: New York 1999).

Recent reports suggest that only 25% of all sexual assault cases lead to the identification of the perpetrator because the problem of co-amplification of DNA in such samples causes most STR based human identification to be ambiguous.

In a complementary embodiment where very few sperm are present in the sample but the dominant cell type are epithelial cells from the vagina, then one can use the antibody approach (with or without holographic optical trapping (HOT)) to first separate out the epithelial cells from sperm by causing the epithelial cells to adhere to the epithelial cell specific antibody coated substrate. In such a situation, the sperm will remain in the supernatant and can be either directly used for cell lysis and extraction. If further purity is needed, they can be separated by using HOT in parallel with the antibody approach. A variety of epithelial cell specific markers especially those from the human vagina, are present for use in this approach. New and novel markers which are constantly being discovered to target/identify various cell types including vaginal cells, can be used. A combination of antibodies might also be used to separate the epithelial cells from sperm in this embodiment. Similarly an antibody free binding approach using common ligand receptor binding may also be used.

The present invention will improve purity in forensic samples to be analyzed through better separation of sperm from contaminating cells, thereby increasing the efficacy in downstream PCR-based STR readouts. In addition, the proposed method is amenable to automation which current methodologies do not allow.

Thus, the present invention relates to a method and apparatus of sorting objects including providing a sample having wanted objects and unwanted objects; coating a surface of a sample holder with an antibody; eluting the sample and placing the eluted sample on the sample holder; binding an antigen in the wanted objects with the antibody on the surface of the sample holder to sort the objects into wanted objects and unwanted objects; separating the wanted objects; removing the unwanted objects; and performing PCR-based STR analysis on the wanted objects. In one embodiment, holographic optical trapping is used to sort the wanted objects from the unwanted objects. In one embodiment, the wanted objects are sperm and the antibody is a human sperm specific antibody. In another embodiment, the STR readout uses single cell PCR based amplification. In other embodiments, the binding is direct or indirect such as using secondary antibodies instead of using primary antibodies alone. In another embodiment, ligands are used to bind to object-specific macromolecules (such as cell surface receptors).

There has thus, been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the different purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to a method and apparatus of sorting objects in DNA analysis, using binding methods, and/or holographic optical trapping (HOT).

Antibody Method

In one embodiment, an antibody coated substrate is used to sort objects such as sperm cells. In general, the present embodiment can operate either in stand-alone mode or in conjunction with holographic optical trapping (HOT) to separate sperm from contaminating cells, and uses an antibody-coated substrate where the antibody selectively recognizes a surface antigen on the human sperm.

Alternatively, another choice of antibody could be one that targets the H—Y antigen typically found on male determining spermatozoa.

Figure 1:
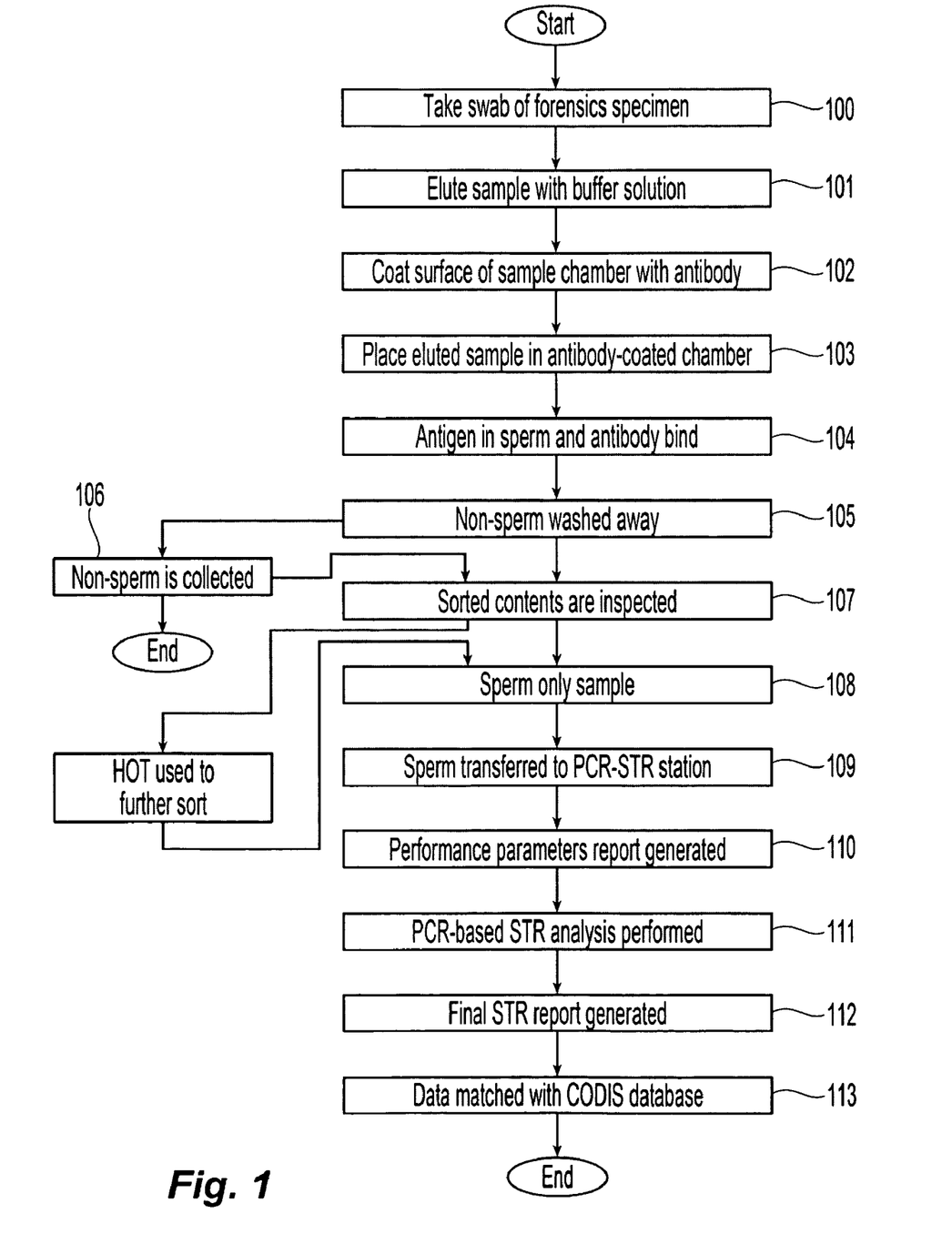
FIG. 1 is a flow chart of the steps in a method of sorting objects, according to one embodiment consistent with the present invention.
Figure 2:
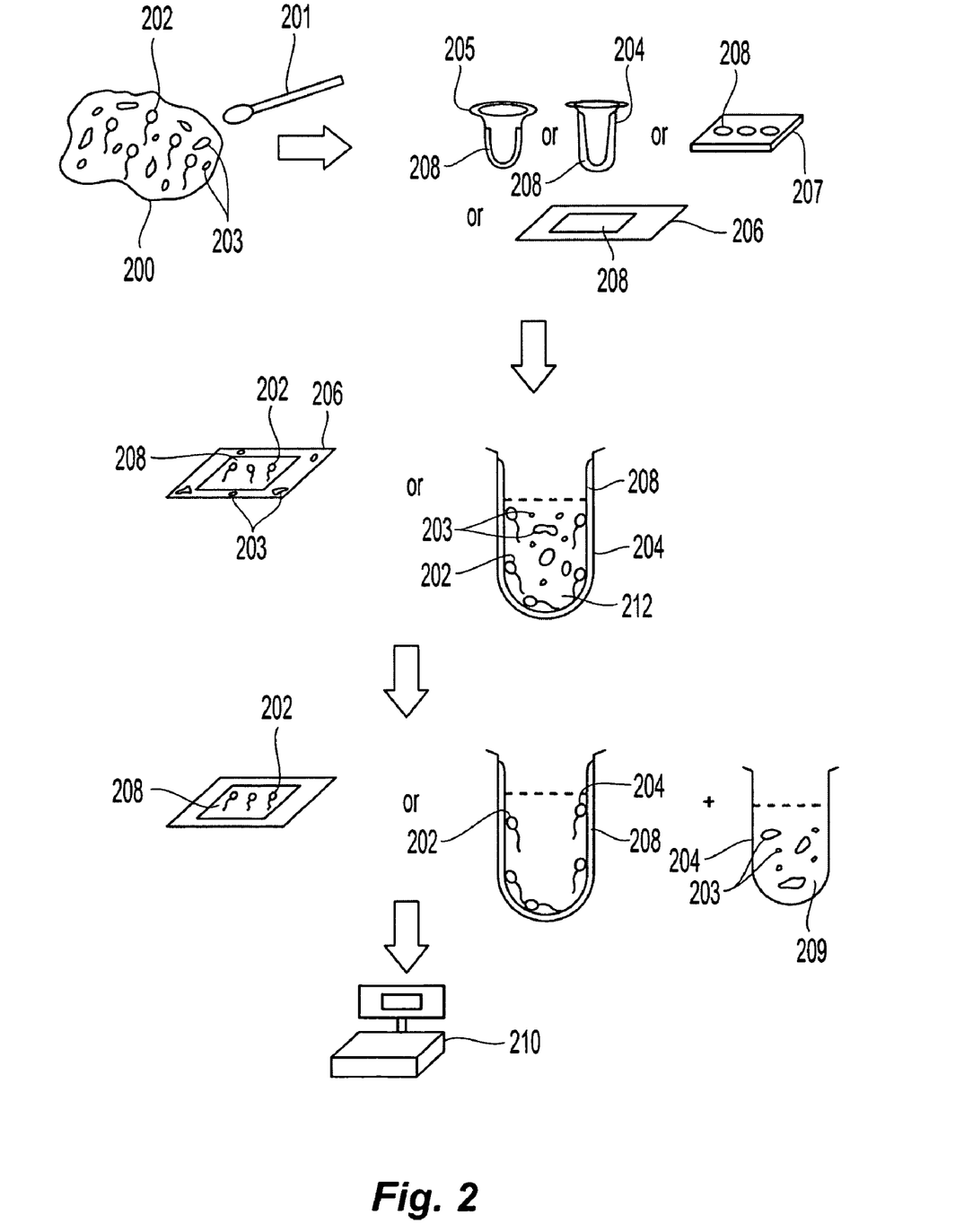
FIG. 2 depicts the apparatus and method of sorting objects of FIG. 1.

Specifically, according to one embodiment of the present invention, the following steps can be taken, as shown in FIGS. 1 and 2, to use an antibody method and apparatus to sort sperm from contaminants and to determine the DNA of a person(s) in a forensics case.

In step 100, a sample 200 is prepared by taking a swab 201 of a forensics specimen, from a victim of sexual assault, for example, and the sample 200 is eluted using a buffer solution 212 (see FIG. 2) in step 101.

The eluted samples 200 typically contain sperm cells 202 from the assailant(s), epithelial cells from the victim, and other contaminants 203, for example.

In step 102, the surface of a test tube 204, an Eppendorf container 205, glass slide 206, microfluidic chip 207, or other container (platforms) intended for sperm separation, are coated with a human sperm specific antibody or another biomolecule such as ligands, peptides, proteins, 208 etc., that would bind to the corresponding binding partner on the sperm. The sperm specific antibody coating 208 can be applied to any surface or sample chamber—i.e., test tube 204, Eppendorf container 205, glass coverslip/coverslide 206, chip 207. Various well established techniques exist for attaching antibodies and peptides, proteins, ligands or other biomolecules to a glass substrate. The surface coating may be applied over the entire internal wall/area of a container (i.e., test tube 204, Eppendorf 205) or on only specific areas or patches on the glass coverslip 206 or chip 207, for example.

In step 103, the eluted forensic sample 200 to be analyzed is placed in the antibody-coated sample chamber/container 204-206 via pipetting or other active mechanism such as a pump, or passive mechanism such as gravity flow, for example.

Figure 3A:
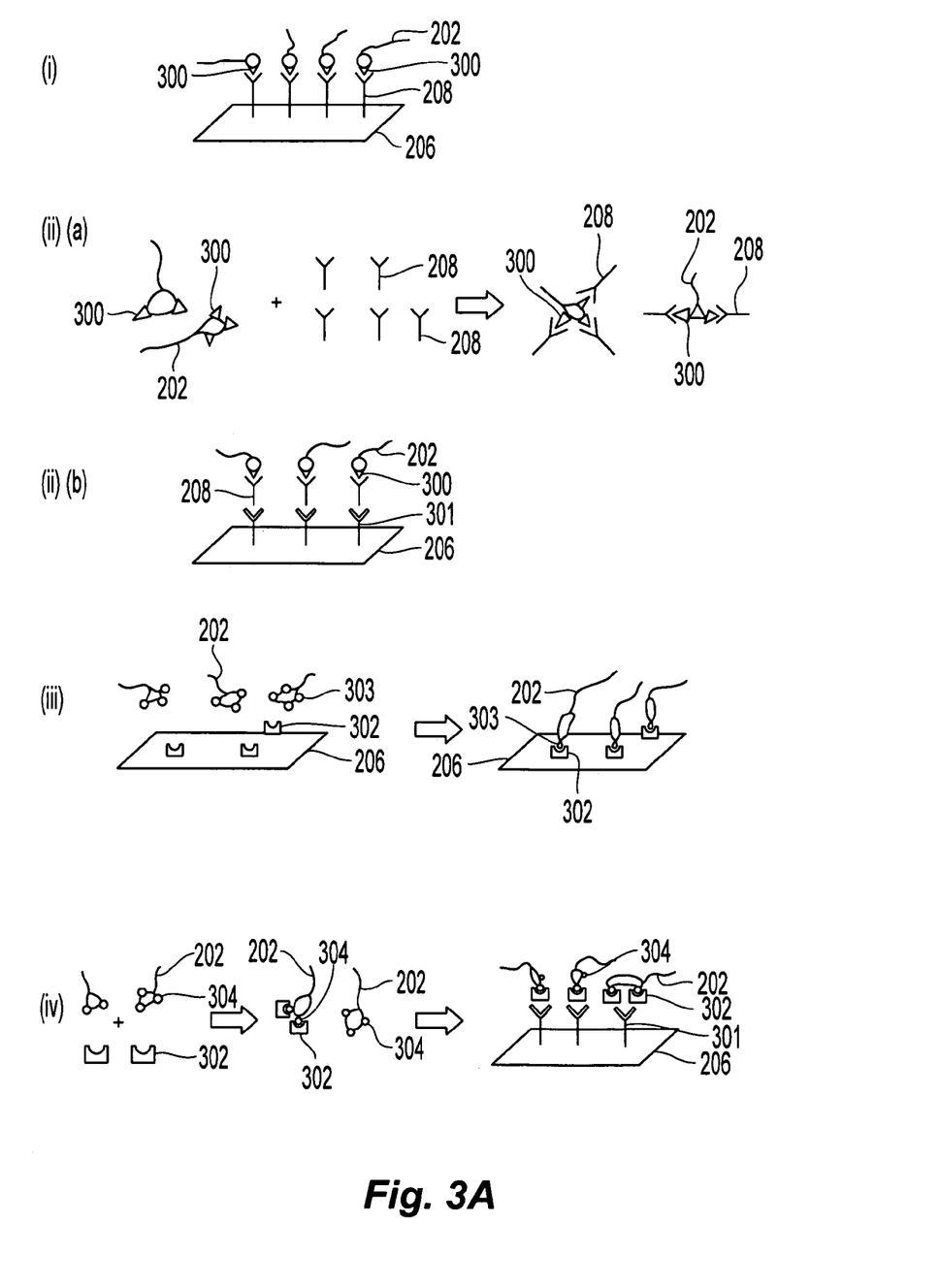
FIGS. 3A and 3B depict the apparatus and method of sorting objects according to other embodiments consistent with the present invention.

In step 104, the antigen 300 (see FIG. 3A(i)) (on the sperm 202) and sperm specific antibody 208 (as might be on the surface of the container 204-206), are allowed to bind. Thus, the antibody 208 directly recognizes the antigen(s) 300 on the cell surface of the sperm 202, and selectively binds to the surface antigen 300 while epithelial and other contaminating cells 203 remain unbound. The antibodies 208 which can be utilized to target sperm antigens 300 can be full length or cleaved or even short peptides that recognize the epitope on the sperm 202 surface. In addition, one can use binding partners of the sperm 202 surface receptors to capture sperm 202 from a mixed cell sample 200.

In step 105, the non-sperm (i.e., non-adhering cells or contaminants 203) are gently washed away from the surface of the sample chamber 204-206 using a suitable buffer solution of desired pH and salt concentration or sperm elution buffer 209 (a couple of washes may be needed), and collected in step 106 if desired, leaving behind only antibody bound sperm cells 202 for downstream analysis (see also FIG. 3A(i)). Depending on the number of sperm 202 captured on the surface of the substrate 204-206 which is required for analysis, the wash steps may be repeated.

In step 107, the sorted contents (i.e., antibody bound sperm 202) are inspected, scanned, and the quality (purity) visualized. This can be done (although not limited to) using either brightfield microscopy (morphology-based identification) or using fluorescent tags to identify sperm cells 202 where morphology may have been altered during the handling process. Fluorescence will also make image processing of the sperm 202 identification easier (since fluorescence offers better contrast than brightfield images) and faster.

In step 108, the sperm cells 202 can then be lysed and the sperm-containing sample chamber 204-206 can be transferred to a station 210 in step 109, where in situ PCR followed by STR forensic analysis, takes place.

Alternatively, in step 108, the bound sperm cells 202 can be released from the antibody coated surface of the sample chambers 204-206 using cleaving agents, or by altering/exchanging buffer solution (such as altering buffer pH to affect antigen-antibody binding) or by altering the salt concentration to affect the effective charge shielding, for example. The sorted sperm 202 can settle by gravity in the sorting container 204-206, or if needed, further pelleted down by centrifugation before moving the chamber 204-206 with sorted sperm cells 202 to the STR analysis performing PCR platform 210, in step 109.

It is to be noted that the ability to carry out the sorting in open or closed containers 204-206 offers flexibility in platform design and use with existing instruments. The ability to carry it out in closed chambers offers the additional advantage of avoiding any contamination in the pre-PCR handling process.

In step 110, a result report may be generated with sperm number, level of purity of the sample 200 tested, and other relevant performance parameters. These reports prior to actual PCR-based STR analysis in step 111 will provide better quality control in the forensic analysis. A visualization method like HOT (described further below) offers the advantage of keeping track of intermediate steps leading up to the final result.

PCR-based STR analysis is performed (step 111) to identify the person whose DNA matches the DNA of the sperm 202. PCR-based STR analysis may also be performed on the contaminants or unwanted objects, such as the epithelial cells of the victim, for cross-checking the validity of a filed criminal charge. The PCR-based STR analysis is in itself well-known in the art and has been broadly commercialized, and thus, not discussed in any detail herein.

Multiple PCR reactions can be carried out at any given time on one machine 210. However, to avoid DNA loss during transfer from chip to tubes, the PCR may be carried out on-chip 207 using flatbed thermocycles.

In step 112, a final STR report is then generated for the sperm 202 analyzed, and statistics generated on the STR profile.

In step 113, the resulting data is matched with the CODIS database for human identification if it is meant for forensic use, for example.

In another embodiment consistent with the present invention, steps 100-103 remain the same. However, in step 104, the antibody 208 on the substrate 204-207 is an anti-IgG which then recognizes the antibody 208 bound to the sperm-specific antigen 300 (see FIG. 3A(ii)(a)). Thus, the antibody 208 on the surface of the substrate 204-207 could be an anti-immunoglobulin antibody 208 which in turn recognizes the monoclonal antibody targeted against the sperm specific surface antigen 300. In cases where very few sperm 202 are present in a forensics sample 200 containing other contaminating cells 203, one can even use multiple sperm specific antibodies 208 in tandem, to select and sort the sperm 202 for downstream analysis while the anti-immunoglobulin surface antibody may remain the same.

In the two-step binding process of this embodiment, in Step I, the sperm-specific antigen 300 is recognized by a specific antibody 208. This antibody 208 which is now bound to the sperm 202 surface will be recognized by a secondary (2°) antibody, such as an anti-IgG (see FIG. 3A(ii)(b)).

Step I (see FIG. 3A(ii)(a)) can be carried out in buffer solution in an Eppendorf container, incubating the sperm 202 in the presence of excess antibody 208. Excess antibody 208 can then be washed off by a simple centrifugal spin. The antibody 208 labeled sperm 202 is then recovered for Step II (see FIG. 3A(ii)(b)) which may be performed on a solid support (substrate) 206, for example.

In Step II, the primary antibody (1°) 208 is received in the secondary antibody (2°) 301 on the support 206. In this second situation where a secondary antibody 301 is used to capture the sperm 202, the secondary antibody 301 (depending on available binding sites) could capture multiple sperm cells 202. The surface density of the secondary antibody 301 can be optimized by keeping steric hindrance in mind. The secondary antibody 301 could be an IgG or an IgM, for example, where an IgM is a pentamer with more binding (ten) sites or an IgG which has two binding sites per molecule.

Thereafter, the steps, such as steps 105-113, remain substantially the same, with the sperm 202 being inspected and prepared, for final STR analysis to determine the DNA of the sperm holder.

In another embodiment consistent with the present invention, steps 100-103 remain the same, but in step 104, instead of immobilizing antibodies 208 on the substrate 206, for example, to capture sperm 202 either directly or indirectly, as described in the previous embodiments, one can immobilize ligands 302 (typically small molecules) on the substrate 206, for example, using various methods which are commercially known, such that the ligands 302 are recognized by cell surface receptors 303 on the sperm 202 surface (see FIG. 3A(iii)), thus, effectively sorting the sperm 202 from contaminants 203.

Thereafter, the steps, such as steps 105-113, remain substantially the same, with the sperm 202 being inspected and prepared for PCR-based STR analysis.

In yet another embodiment consistent with the present invention, steps 100-103 remain the same, but in step 104, an indirect approach—as shown in FIG. 3A(ii)(b)—is used to implement a two-step process for sperm 202 capture. The first step involves use of a ligand 302 to bind the sperm-specific proteins, peptides, cell surface molecules (glycopeptides, etc.) 304. Thereafter, the second step is then used to capture the ligand 302 bound sperm 202 using an antibody 301.

Thereafter, steps 105-113 remain substantially the same, with the sperm 202 being inspected and prepared for PCR-STR analysis.

It is noted that standard bioconjugation chemistries are available for attaching antibodies 208 on a substrate 205-207 which can be glass or other materials like plastic. Antibody conjugation on the substrate can be via utilization of common covalent or non-covalent linkage or via adsorption.

Thus, all the approaches discussed herein can be envisioned in other formats outside of immobilization on a solid support like glass or plastic 206. This would include substrates of varying geometries such as a flat substrate (in single or multi well format) or a curved surface such as that of an Eppendorf tube.

Figure 3B:
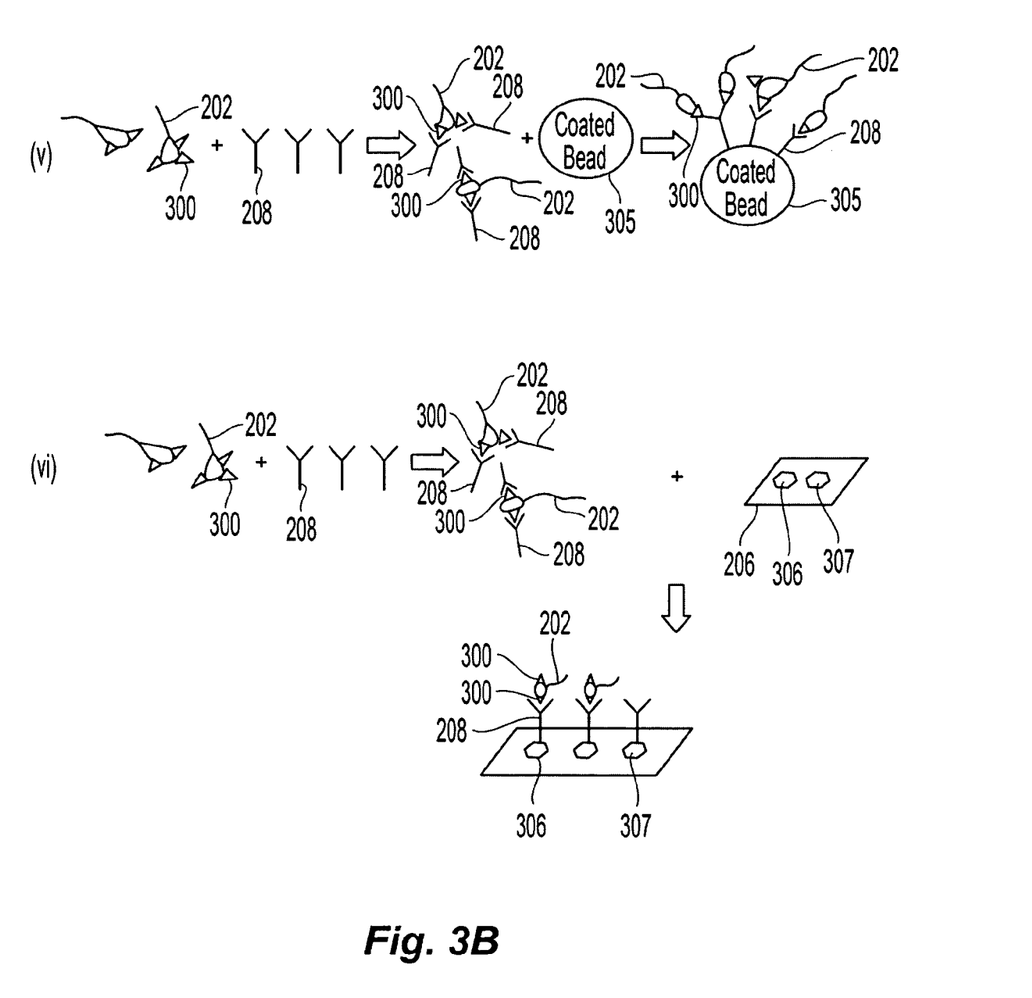

In another embodiment, as shown in FIG. 3B(v), an alternative apparatus may include using beads (i.e., silica, magnetic, polystyrene beads) 305 coated with antibodies to bind directly or indirectly to the sperm 202 for sperm capture.

Further, in yet another embodiment consistent with the present invention as shown in FIG. 3B(vi), one can utilize the strong affinity between Protein A 306 and Protein G 307 towards binding antibodies 208 to provide an alternative form of the invention. Therefore, in the embodiments discussed above with respect to indirect methods of binding, instead of using secondary antibodies 301 to recognize the primary antibodies 208 which are sperm 202 bound, one can have beads 305 and/or Protein A 306 or Protein G 307, recognize and capture the sperm 202 bound primary antibodies 208.

Thereafter, steps 105-113 remain substantially the same, with the sperm 202 being inspected and prepared for PCR based STR analysis.

Holographic Optical Trapping

Figure 4:
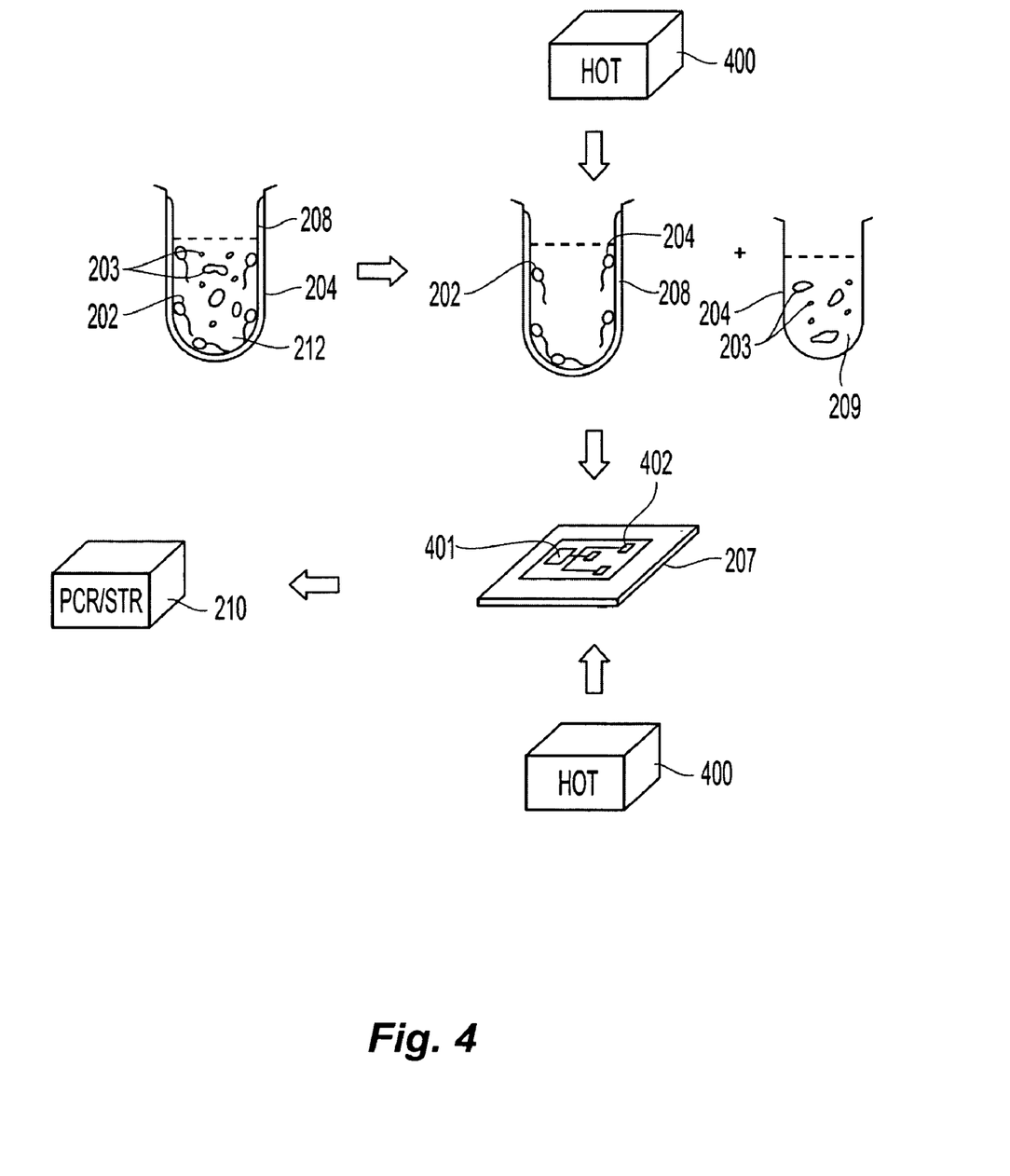
FIG. 4 is a schematic of a method and apparatus of sorting objects using holographic optical trapping, in another embodiment consistent with the present invention.

In another embodiment consistent with the present invention, for forensic samples where an additional level of purity (in sorting sperm, for example) is needed beyond antigen-antibody binding based sorting or protein-ligand binding based sorting as described above, HOT 400 may be utilized after performing steps 101-103 above (see FIG. 4).

The HOT apparatus is well known in the art, and is described in detail in, for example, U.S. Pat. No. 6,055,106, to Grier et al., which is herein incorporated by reference in its entirety.

Thus, HOT can be used in parallel with the antibody approach described above, where a variety of cell specific markers, especially those that recognize and bind human sperm, are present for use and sorting. New and novel markers which are constantly being discovered to target/identify various cell types including epithelial cells can be used. A combination of antibodies might also be used to separate the epithelial cells from objects/sperm in this embodiment. This invention will resolve existing challenges in incomplete separation of sperm DNA from epithelial cell DNA which leads to coamplification of wanted and unwanted DNA. This in turn leads to mixed STR profile generation rather than a unique STR profile.

Specifically, using HOT is advantageous where very few objects/sperm are present in the sample, and the dominant cell type are epithelial cells (contaminants) from the vagina. In that case, one can use the antibody approach described above (with or without HOT) to first separate out the epithelial cells from sperm by causing the epithelial cells to adhere to the epithelial cell specific antibody coated substrate (i.e., glass slide or microfluidic chip). In such a situation, the sperm will remain in the supernatant and can be either directly used for cell lysis and extraction.

Thus, after the antibody labeled sperm cells on the substrate are bound, further sorting of non-adhering contaminants (which might not have been fully removed via washing with buffer) will be cleaned out using optical trapping, leaving behind only sperm cells on the substrate. Thus, in this embodiment, HOT 400 is used to sort the objects (i.e., sperm) in addition to, or alternatively to, the antibody method, from contaminating cells in a sample.

Thereafter, steps 105-113 remain the same as described in FIG. 1.

Microfluidics Chip and Single-Cell PCR-STR Analysis

Note that in the previous embodiments, a microfluidic chip 207 may be used. The use of a microfluidic chip in sorting objects is described in detail in copending application entitled "Methods and Apparatus in Sorting Objects in DNA Analysis" filed Sep. 11, 2008, the contents of which are herein incorporated by reference in their entirety.

As described therein, HOT 400 is used to sort objects such as sperm, and taken with the antibody method described herein (see FIGS. 2 and 4), and the use of a microfluidics chip 207 containing an input chamber 401 and individual output chambers 402, the sperm 202 can be sorted into the individual chambers 402 using HOT. In this embodiment, HOT is used to separate the sperm cells 202 in the forensics sample 200, by visual (microscope or monitor) inspection, from other contaminating cells 203, by moving the optically trapped sperm 202 from one area of the microfluidic chip 207 into individual chambers 402 on the same chip 207, for example.

Thereafter, PCR-based STR analysis is performed at a PCR 210 station to identify the person whose DNA signature matches that of the sperm, similarly to steps 105-113 described above.

Conventionally, a significant number of cells were required to get a reliable STR readout signal. However, with the gentle method of HOT-based sperm separation and improved sensitivity, a more reliable separation of sperm from contaminating non-sperm cells can be performed, and one can scale down the sample collection in terms of number of sperm cells needed for PCR-based STR analysis from about 200 (as is required in conventional methods), to a few cells, or even to the level of single cell PCR—greatly increasing its efficiency (see chambers on chip). This in turn offers all the advantages of single cell PCR in forensics analysis which include the higher probability of identifying assailants in a multiple sexual assault case or in cases where very few sperms are available for standard bulk PCR analysis.

Thus, single-cell PCR can be carried out on each individual sperm in chambers, using standard PCR methods (lysing individual sperm in individual chambers in a multi-chamber chip, extracting the DNA and simultaneously amplifying the DNA from single cells in all chambers).

In particular, the chip is placed on a flatbed thermocycler, where the extracted DNA is amplified by PCR using STR primers which are commercially available for forensic cases. Alternatively, a custom-designed appropriate primer can be used where forensic cases are not involved. The number of thermocycles is increased to leave enough DNA from the individual cells at the end of the PCR cycling.

DNA extraction may be performed by centrifugation (post cell lysis) or by attaching to magnetic beads, where the DNA is eluted from the beads (magnetic or others) by changing the pH (altering the charge on the DNA, i.e., to affecting binding of the DNA to the beads).

Once PCR is completed, standard STR analysis can be carried out. This involves running gels on the amplified DNA for STR readouts where each PCR reaction corresponds to amplified DNA from a single sperm. Commercially available instruments may be used for this purpose.

Thus, in addition to standard PCR/STR analysis in tubes or on plates, in one embodiment, the analysis can also be performed on a single chip (on-chip PCR). In this embodiment, the sperm in sample can be lysed in situ, or the sperm in each well or chamber can by lysed and passed through a filter to separate the cell debris from the DNA, and only allow DNA to proceed to the next chamber, where PCR (bulk) is run (i.e., on DNA from several sperm). The chamber is connected to an on-chip PCR device with the capability of STR readout.

As stated above, a final STR report is then generated for each individual sperm analyzed, and statistics generated on the STR profile. The resulting data is matched with the CODIS database for human identification if it is meant for forensic use, for example.

The virtue of individual sperm (single cell) STR readout is that, it:

(1) increases the likelihood of detecting multiple assailants (if involved in a sexual assault case) based on the statistical significance of the STR readout (well-established by standard regulations); and (2) it offers the ability to analyze those crime cases where obtaining 200 sperm cells is a challenge due to the limited availability of sample sperm cells, thus, enhancing the chance of ruling out incriminated persons in a sexual assault case, for example.

Thus, one can envision revolutionizing the nature and scope of STR based forensics offering solutions to more cases where sufficient sample collection posed a problem before. Analysis on one or few cells will cut down on sample collection time as well.

In rare cases, where allele dropout is a problem and an STR profile (based on standard bulk PCR analysis) could not be matched to the CODIS database (the dominant allele masking the other), there is a greater likelihood of matching an STR signature as obtained from single cell PCR to the database with relevant statistical calculations, to arrive at the needed probability.

By analyzing STR on individual sperm cells and repeating the analysis for a number of sperm cells from a given sample on a one-by-one basis, one can now reliably solve sexual assault cases where multiple assailants are involved such as in a gang-rape crime. Thus, no deconvolving is needed in resolving STR profiles of individuals from a cell-mixture set.

Further, single-cell PCR based forensics will offer the ability to perform repeat measurements and more statistically reliable data can be obtained in solving a crime case. Still further, as described above In step 108, the primary and/or the secondary antibodies maybe fluorescently labeled and the throughput for automated sperm separation via HOT will be faster since image recognition of fluorescent samples typically work faster due to better contrast.

The methods proposed here are compatible with automation and multiplexing—i.e., running multiple forensic sample analysis thereby increasing throughput; and further, can be integrated with robotics where multiple crime samples can be eluted, separated and tested at the same time thereby increasing throughput. Coupling with robotics includes additional advantages since it is platform independent—i.e., can be carried out on glass slides (glass coverslips) or in test tubes or in Eppendorfs or even in 96 well format (given that there are now machines such as flat bed thermocyclers that can carry out PCR in 96 well or higher well formats, in situ PCR is possible using such separation).

This methodology is compatible with in situ PCR on forensic samples. Therefore, all advantages of in situ PCR will be valid such as:

(i) to reduce chance of contamination since in situ PCR will involve fewer steps and avoid transfer of samples from one container to another; and (ii) cut down cost of such forensic analysis by limiting supply cost that is likely involved with more steps and transfer of samples.

The invention described herein is better than the commonly used method of differential extraction which suffers from several disadvantages such as mixing of male and female fractions and often immature cell lysing. In addition, differential extraction which is the widely practiced method for separating sperm from epithelial cell DNA is labor intensive, time-consuming and lacks scope for automation. The current invention circumvents these problems and offers better quality and reliability in the separation process prior to STR analysis.

While alternative techniques such as the use of a double membrane filter in which a distinctly defined rigid pore size of the filter was designed to allow DNA from digested epithelial cells to pass through while trapping sperm (see Ladd Carl et al., "Development of a high throughput method to isolate sperm DNA in sexual assault cases", August 2006), this method was argued to be too harsh and caused immature lysing of sperm. Antibody-antigen binding or protein-ligand binding based sperm sorting prevent the harshness of mechanical separations.

Other alternate methods have used a similar approach where a nylon mesh membrane was used instead of one with a rigid pore size. Such membrane-based separations can be partially automated or offer better speed than manually operated ones via coupling of a vacuum pump to the system. However, the addition of the pump decreases the resolution in separation—i.e., unwanted components from the mixed cell sample can get sucked into the membrane separated portion.

Further, the present invention has the advantage that it can be operated via direct microscopic visualization which offers better control on the sample quality (purity).

Another method in the field of forensic sample analysis for cell type separation is called laser capture micro-dissection. While this method works better than differential extraction in separating sperm from epithelial cells, it is expensive, requires additional intermediate steps for cell fixation and works best when cells are separated from one another and are in single layer rather than when they are in clusters. Therefore, none of the existing techniques/methods satisfy all the criteria for epithelial from sperm cells separation. The invention described here either in its stand alone mode or in conjunction with HOT can overcome the pitfalls and difficulties of existing techniques and is amenable to complete automation.

While the invention here is particularly described in the context of solving sexual assault forensic cases (which comprise about ⅔ of forensic cases (see reference, "Forensics DNA Typing", 2$^{nd}$ edition by James Butler), its application in the field of forensics extends beyond that wherever there is a need for cell type separation.

In other embodiments, since most cells have cell type specific surface markers, it is possible to extend the antibody based separation into areas outside of forensics such as in basic research or in cancer diagnostics.

In the field of forensics, one extension of this invention is the utilization of this antibody based cell separation method in DNA-based parentage testing. Such testing is necessary to identify the biological father of the embryo or fetus in the event of a failed or aborted pregnancy which occurs frequently after sexual assault. Fetal remains or aborted material is used as the source of fetal DNA. However if recognizable fetal parts cannot be confidently identified for parentage testing, microscopic examination of fixed tissue from post-mortem samples or genetic amniocentesis are the only ways to distinguish maternal (decidual) vs. fetal (chorionic villi) components of the recovered products. However, once again, conventionally, the cell separation is far from being perfect. However, with the present invention, antibody-based separation in conjunction with HOT could separate the maternal and chorionic villi components before PCR amplification of the extracted DNA. This approach offers the ability for direct visualization of the samples wherever needed.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of sorting objects comprising:
providing a sample having wanted objects and unwanted objects;
coating a surface of a sample holder with an antibody;
eluting said sample and placing said eluted sample on said sample holder;
binding an antigen in wanted objects in said sample with said antibody on said surface of said sample holder to sort said objects into bound wanted objects and unbound unwanted objects;
separating said wanted objects from said unwanted objects by removing said unwanted objects from a surface of said sample holder, leaving behind antibody-bound wanted objects on said surface of said sample holder;
inspecting and identifying said wanted objects, and determining a level of purity of said wanted objects;
releasing said wanted objects from said surface of said sample holder;
removing said wanted objects from said surface of said same sample holder using holographic optical trapping; and
performing single cell PCR-based STR analysis on said wanted objects in individual output chambers on said same sample holder.

2. The method of claim 1, wherein said wanted objects are cells, including sperm cells, said antibody is a human sperm specific antibody, and said unwanted objects are contaminants.

3. The method of claim 1,
wherein said PCR is bulk PCR on multiple sorted objects of a same type; and
wherein said PCR performing step is compatible with automation and multiplexing.

4. The method of claim 1, further comprising:
performing said identifying step using one of brightfield microscopy or fluorescent microscopy.

5. The method of claim 1, further comprising:
binding an antigen to a primary antibody; and
binding said primary antibody to a secondary antibody.

6. The method of claim 1, further comprising:
immobilizing ligands on said sample holder;
binding cell surface receptors on a surface of said wanted objects with said ligands.

7. The method of claim 1 , further comprising:
binding a ligand to object-specific organomolecules; and
capturing said ligand bound object using an antibody.

8. The method of claim 2, wherein said sample holder contains beads coated with said antibody to bind, one of directly or indirectly, to said wanted objects.

9. The method of claim 8, further comprising:
binding said antigen to a primary antibody; and
binding said primary antibody to a secondary antibody, wherein said bead is coated with one of Protein A or Protein G, and
wherein said bead recognizes and captures said wanted objects bound to said primary antibody.

10. The method of claim 1, further comprising:
coating one of Protein A or Protein G on a surface of said sample holder;
binding said antigen to a primary antibody; and
binding said primary antibody to a secondary antibody;
wherein said Protein A or Protein G recognizes and captures said wanted objects that are antibody labeled.

11. The method of claim 1, wherein said sorting step using antibody-based sorting in conjunction with said holographic optical trapping separates cells of different types based on antigenic display.

12. The method of claim 1, further comprising:
generating a report with respect to said level of purity of said wanted objects prior to said PCR-based STR analysis.

13. The method of claim 1, wherein said same sample holder is an optically transparent microfluidics chip.

14. The method of claim 1, wherein said single cell PCR-based STR analysis is performed on said unwanted objects.

15. The method of claim 1, wherein said separating step includes washing said wanted objects from said sample holder.

16. The method of claim 2, wherein said removing step includes lysing said wanted objects from said sample holder.

17. The method of claim 2, wherein said removing step includes one of utilization of cleaving agents, altering/exchanging buffer solution, or altering a salt concentration to affect an effective charge shielding or charge switching.

18. The method of claim 17, wherein said removed wanted objects one of settle by gravity in said sample holder, or are pelleted down by centrifugation.

19. The method of claim 1, wherein said sorting of said wanted objects and unwanted objects is carried out in one of open or closed containers.

20. The method of claim 1, wherein said sample holder is a chip, and said single cell PCR-based STR or other DNA analysis is carried out on-chip.

21. The method of claim 1, wherein said inspecting step is performed using holographic optical trapping.

22. The method of claim 12, further comprising:
generating a final STR report for the wanted objects analyzed; and
generating statistics on an STR profile.

23. The method of claim 22, further comprising:
matching said STR profile data with a database for human identification.

24. The method of claim 5, further comprising:
incubating said wanted objects in excess antibody;
washing off said wanted objects by centrifugal spin; and
recovering said antibody labeled wanted objects on said sample holder.

25. The method of claim 5, wherein said secondary antibody is used to capture said wanted objects.

26. The method of claim 1, wherein said sample holder is one of optically transparent glass or plastic.

27. The method of claim 13, wherein said microfluidics chip contains an input chamber and said individual output chambers; and
wherein each of said wanted objects are sorted using said holographic optical trapping, into each of said individual output chambers.

* * * * *